(12) United States Patent
Böck

(10) Patent No.: US 6,319,236 B1
(45) Date of Patent: *Nov. 20, 2001

(54) UNIVERSAL OUTLET FOR FILTER UNITS

(75) Inventor: Daniel C. Böck, Beverly, MA (US)

(73) Assignee: Millipore Corporation, Bedford, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/187,717

(22) Filed: Nov. 6, 1998

(51) Int. Cl.$^7$ .................................................. A61M 5/31

(52) U.S. Cl. ..................... 604/240; 604/190; 604/243; 604/533; 604/905

(58) Field of Search ................................ 604/240, 403, 604/405, 406, 190, 199, 533, 534, 535, 241, 242, 243, 236, 237, 238, 252, 256, 905; 128/912

(56) References Cited

U.S. PATENT DOCUMENTS

| | | |
|---|---|---|
| 2,857,913 | 10/1958 | Miskel . |
| 3,601,151 * | 8/1971 | Winnard . |
| 3,882,026 | 5/1975 | McPhee . |
| 3,978,857 * | 9/1976 | McPhee . |
| 4,043,335 * | 8/1977 | Ishikawa . |
| 4,061,143 * | 12/1977 | Ishikawa . |
| 4,127,131 * | 11/1978 | Vaillancourt . |
| 4,198,974 | 4/1980 | Heavner et al. . |
| 4,296,949 * | 10/1981 | Muetterties et al. . |
| 4,597,758 | 7/1986 | Aalto et al. . |
| 4,732,672 | 3/1988 | Kiang et al. . |
| 5,006,114 | 4/1991 | Rogers et al. . |
| 5,037,544 | 8/1991 | Snyder . |
| 5,066,286 | 11/1991 | Ryan . |
| 5,066,287 | 11/1991 | Ryan . |
| 5,071,413 | 12/1991 | Utterberg . |
| 5,075,080 * | 12/1991 | Sanders . |
| 5,184,652 | 2/1993 | Fan . |
| 5,203,775 | 4/1993 | Frank et al. . |
| 5,217,590 | 6/1993 | Lauer et al. . |
| 5,294,325 | 3/1994 | Liu . |
| 5,409,477 * | 4/1995 | Caron et al. ................. 604/403 |
| 5,465,938 | 11/1995 | Werge et al. . |
| 5,480,393 | 1/1996 | Bommarito . |
| 5,573,516 | 11/1996 | Tyner . |

(List continued on next page.)

FOREIGN PATENT DOCUMENTS

| | | |
|---|---|---|
| 1 268 914 | 5/1990 | (CA) . |
| 0 351 643 | 1/1990 | (EP) . |
| 0 494 779 | 9/1992 | (EP) . |
| 0 765 727 | 4/1997 | (EP) . |
| 1215361 | 12/1970 | (GB) . |
| 94/13338 | 6/1994 | (WO) . |
| 95/03841 | 2/1995 | (WO) . |
| 96-41649 | 12/1996 | (WO) . |

OTHER PUBLICATIONS

American National Standard ANSI/MIMA MD70.1–1983; "American National Standard for Medical Material–Luer Taper Fittings–Performance"; pp. 7–15.

Primary Examiner—Richard K. Seidel
Assistant Examiner—Jeremy Thissell
(74) Attorney, Agent, or Firm—Nields & Lemack

(57) ABSTRACT

Filter device comprising a filter housing, a filter disposed in the filter housing, an inlet, and an opposed outlet spaced from the inlet, wherein the outlet comprises an extension from the housing, the extension extending longitudinally in the direction of fluid flow and comprising at least a first section having a minimum outer diameter and a second section downstream from the first section and having a terminal end having a maximum outer diameter, the maximum diameter of the second section terminal end being smaller than the minimum diameter of the first section.

15 Claims, 4 Drawing Sheets

U.S. PATENT DOCUMENTS

| | | |
|---|---|---|
| 5,592,948 | 1/1997 | Gatten . |
| 5,613,663 * | 3/1997 | Schmidt et al. . |
| 5,685,855 | 11/1997 | Erskine . |
| 5,730,733 | 3/1998 | Mortier et al. . |
| 5,759,178 | 6/1998 | Wells . |
| 5,776,117 * | 7/1998 | Haselhorst et al. .................. 604/533 |

* cited by examiner

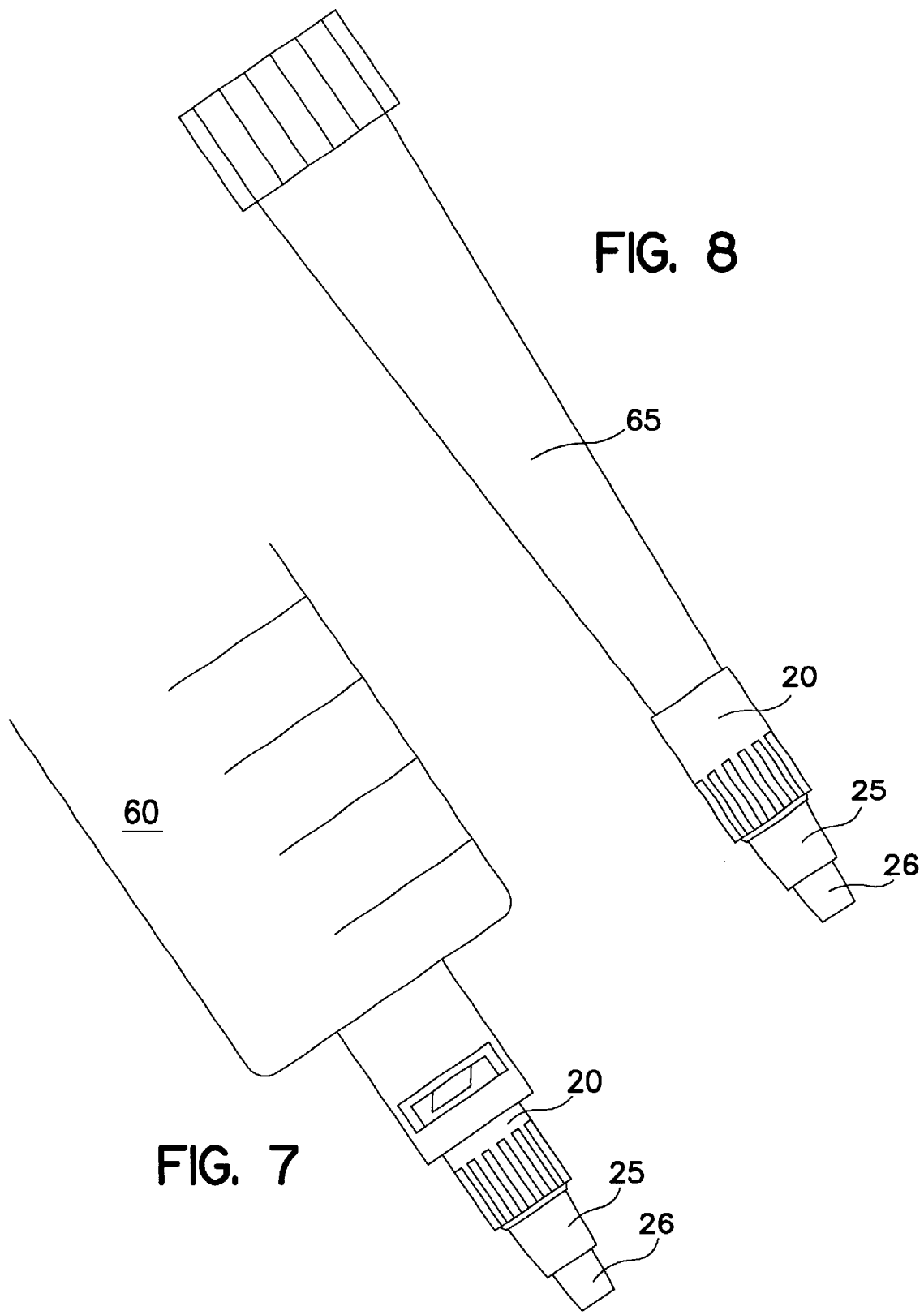

UNIVERSAL OUTLET FOR FILTER UNITS

BACKGROUND OF THE INVENTION

Filtration of solutions is generally desired to remove particles in sample preparation applications, analytical techniques and prior to an instrumentation analysis, for example, or to sterilize a solution in tissue culture applications. Depending upon the volumes that need to be filtered, different syringe driven filter sizes, identified by their filter diameter, are available. These include 4 mm, 13 mm and 25 mm sizes. The 4 mm syringe driven filters are typically recommended for the filtration of volumes less than or equal to 1 ml.

Conventional syringe drive filters have male and female luer taper fittings designed to mechanically connect two medical devices such as a syringe and a needle. As shown in FIG. 1, most conventional syringe driven filters have a female luer lock inlet and male luer slip outlet. The female luer lock inlet ensures that the filter is securely (but removably) attached to the outlet of the syringe so as to prevent leakage and loss of sample while filtration takes place. This is especially critical when low sample volumes are being filtered. The lock is conventional and includes outer annular wings designed to be removably engaged (by twisting) in corresponding thread-like ribs in the outlet portion of the syringe. The internal diameter of the female luer is standardized, according to ANSI specifications, to receive a corresponding standardized male luer such as on a syringe. This standardization ensures that the male and female portions will properly mate. As an alternative to the luer lock design, a friction fit ("luer slip") can be used, especially in low-pressure applications.

Similarly, the male luer slip outlet on the syringe driven filter device allows, for example, a needle to be attached to the outlet of the filter and facilitates a direct injection of a filtered sample into an HPLC (high pressure liquid chromatography) instrument, for autosampler vials or other receptacle for further analysis.

Another conventional syringe driven filter device is illustrated in FIG. 2. This device includes a narrowed outlet or "recorder taper" used in place of the male luer slip of the device of FIG. 1. The recorder taper is narrower than the male luer slip, and thus does not function as a luer (i.e., it does not allow for a friction-fit engagement with a standardized female luer). However, the recorder taper facilitates filtration into small receiving vessels such as HPLC autosampler vials, vial inserts and the wells of microtitre plates. The smaller outlet further minimizes the potential of the filtered sample becoming lodged ("airlocked") through capillary action in the top of the narrow receiving vessel such as an autosampler insert, as the air caught beneath the sample cannot escape to allow the sample to flow to the bottom of the vessel. An additional feature of this design is a very small downstream (internal volume after the membrane) volume attributed to a smaller internal diameter in the outlet. This can be especially important with small sample volumes.

A still further conventional design is shown in FIG. 3. This design is a 4 mm syringe driven filter with a "tube tip" or "tube outlet". A short tube is inserted into the outlet orifice of the standard male luer slip design in order to facilitate the filtration into a small receiving vessel. However, this design suffers from the drawback of having a larger downstream volume by virtue of the length of the tube tip, which is undesirable with small sample volumes.

It therefore would be desirable to provide a filter device such as a syringe driven filter that includes all of the features of conventional devices, but does not suffer from any of their drawbacks.

It further would be desirable to provide a filter device that has multiple outlet features so that a single device can serve multiple laboratory filtration applications, thereby reducing the number of specialized filters the user needs to have on hand.

SUMMARY OF THE INVENTION

The problems of the prior art have been overcome by the present invention, which provides a filter device comprising a filter housing, a filter disposed in the filter housing, an inlet, and an opposed outlet spaced from the inlet, wherein the outlet comprises an extension from the housing, the extension extending longitudinally in the direction of fluid flow and comprising at least a first section having a minimum outer diameter and a second section downstream from the first section and having a terminal end having a maximum outer diameter, the maximum diameter of the second section terminal end being smaller than the minimum diameter of the first section. In a preferred embodiment, the filter device is syringe driven, the inlet is a female luer section, and the first section of the outlet comprises a shortened male luer section.

BRIEF DESCRIPTION OF THE DRAWINGS

FIG. 7 is a side view of one embodiment of the present invention showing a syringe attached to the inlet of the filter device;

FIG. 8 is a side view of one embodiment of the present invention showing a pipette tip attached to the inlet of the filter device;

DETAILED DESCRIPTION OF THE INVENTION

Figure 1:
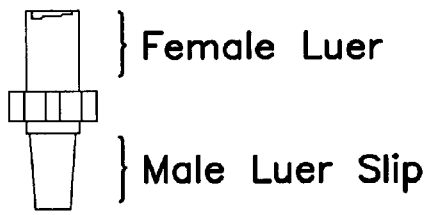
FIG. 1 is a front view of a conventional syringe driven filter device having a female luer lock and a male luer slip.
Figure 2:
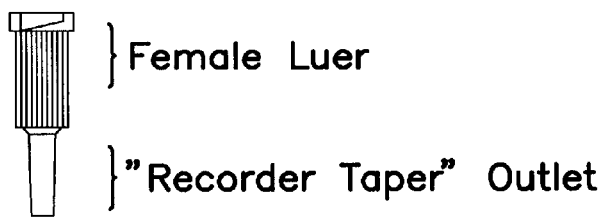
FIG. 2 is a front view of a conventional syringe driven filter device having a female luer lock and a recorder taper outlet.
Figure 3:
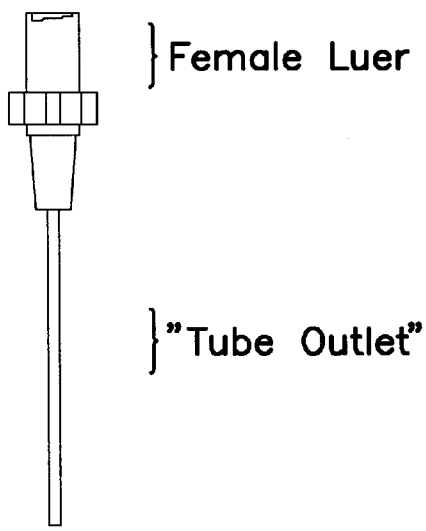
FIG. 3 is a front view of a conventional syringe driven filter device having a female luer lock and a tube outlet.
Figure 4:
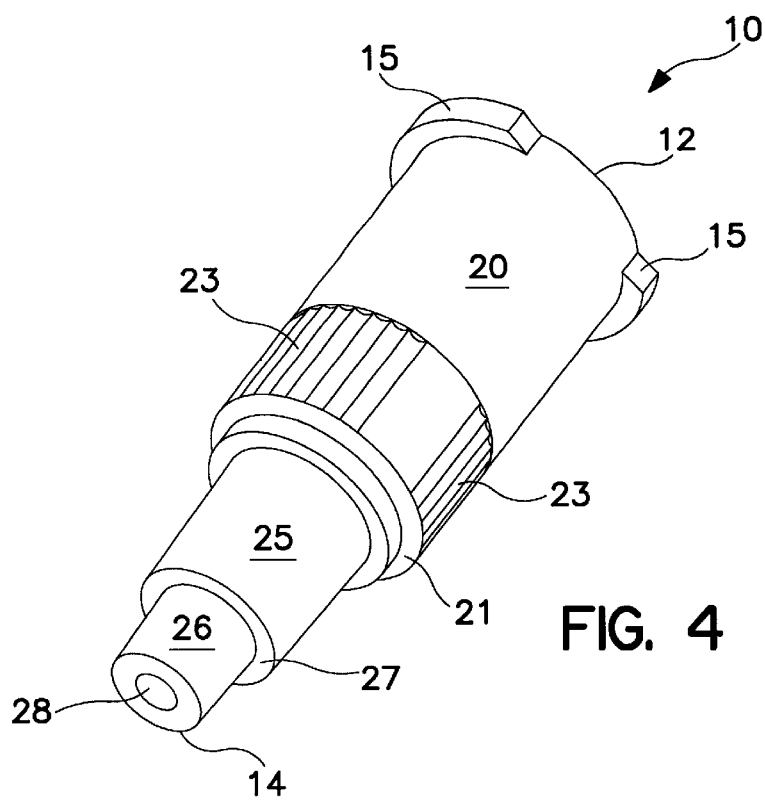
FIG. 4 is a perspective view of a syringe driven filter device according to one embodiment of the present invention.
Figure 5:
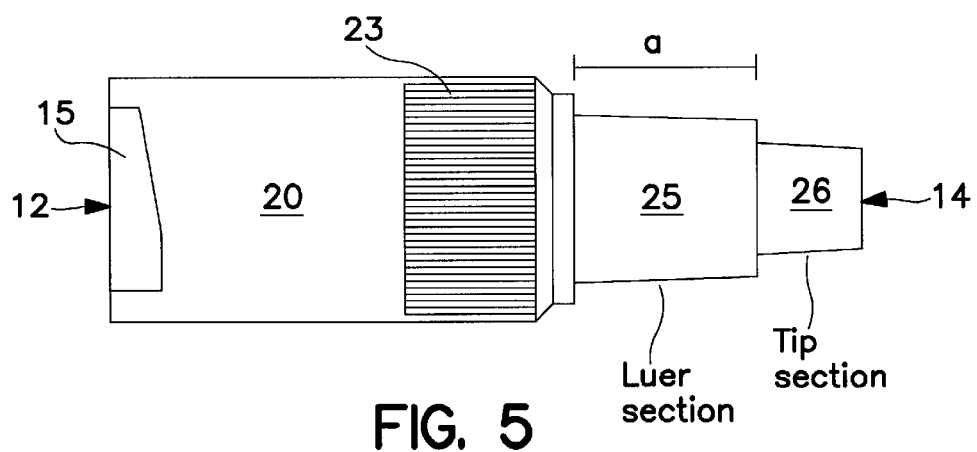
FIG. 5 is a side view of the filter device of FIG. 4.
Figure 6:
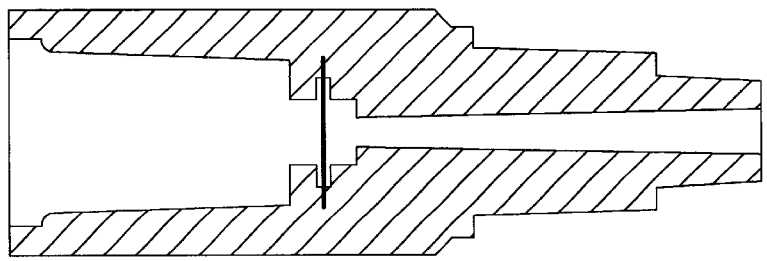
FIG. 6 is a cross-sectional view of the filter device of FIG. 4.

Turning now to FIGS. 4 and 5, there is shown a 4 mm syringe drive filter unit 10 in accordance with one embodiment of the present invention. (Those skilled in the art will appreciate that the filter device of the present invention encompasses any device that utilizes pressure differential across the filter to drive the liquid therethrough, including syringes, pipettors and centrifuge-assisted applications, and that the syringe driven devices illustrated and discussed are exemplary only.) The device 10 includes an inlet end 12 and an outlet end 14 longitudinally spaced from the inlet end 12 in the direction of fluid flow through the device. The inlet end 12 comprises an aperture or opening 30 (FIG. 6)

providing fluid communication into the filter device housing. In a preferred embodiment of the present invention, the inlet end 12 comprises a female luer section designed in accordance with conventional ANSI specifications. A centrally located bore 35 is provided to allow fluid communication between the device 10 and another device containing the sample to be filtered that is to be attached to the female luer in a leakproof manner, such as a syringe 60 (FIG. 7). It is preferred that the female luer include means to effectuate a luer lock, such as outer annular protrusions 15 which are configured to screw into corresponding thread-like ribs in a male luer lock of the syringe 60 or the like. The luer lock prevents both axial and rotational movement of the filter device 10 with respect to the attached device, once engaged. Alternatively, a friction or slip fit is often suitable, such as in connection with the terminal end of a pipette tip 65 as shown in FIG. 8.

Suitably located in the housing 20 of the filter unit 10 is a filter 40. The choice of filters will depend upon the application and is not particularly limited; depth filters, microporous filters, ultrafiltration filters, absorptive filters and any other filters or separations media can be used. Preferably the filter 40 is secured in proximity to the base 21 of the housing 20 in a conventional manner, such as thermally, adhesively, chemically or mechanically such as with compression. An underdrain structure 45 comprising one or more ports is located beneath the filter 40, in the direction of fluid flow, to support the filter and to direct filtrate to flow into the internal axial bore 28 and towards the outlet 14 of the device 10. Those skilled in the art will appreciate that the 4 mm version of the syringe driven filter device 10 is shown by way of example, and that smaller and larger devices, such as 13 mm, 25 mm and 50 mm filters, are within the scope of the present invention. Although in such larger devices the housing 20 configuration changes (e.g., can be disc shaped rather than cylindrical as in the 4 mm embodiment) in order to accommodate the larger filter, the inlet 12 portion and outlet 14 portion are the same.

Optionally formed in the outer surface of the housing 20 such as near the base 21 are a plurality of nubs, grooves, ridges 23 or the like designed to assist the user in handling the filter unit 10. Alternatively, spaced projections, wings or surface textures could be used to provide the same function.

The outlet 14 portion of the device 10 comprises an extension 50 extending longitudinally from the housing in the direction of fluid flow. The extension 50 comprises at least a first section 25 in fluid communication with the housing 20 through the filter and underdrain, the first section 25 having a certain minimum outside diameter. Although the outside diameter of the first section 25 can vary along its length, the minimum outside diameter referred to herein is that portion of the section 25 having the smallest outside diameter. The extension 50 also comprises a second section 26 in fluid communication with the first section 25 and extending in the longitudinally in the direction of fluid flow. In the embodiment shown, the second section 26 extends axially directly from the first section 25 and is contiguous thereto. The second section 26 has a terminal end 47 having a maximum outside diameter that is smaller than the minimum outside diameter of the first section 25.

In a preferred embodiment, the first section 25 is a male luer slip portion tapered and dimensioned in major diameter in accordance with ANSI standards for a male luer, and has an internal axial bore that is preferably centrally located. It is shorter (in the direction of fluid flow) in length than conventional ANSI luers, in order to accommodate the second section 26 without unnecessarily increasing the downstream volume of the device. However, it cannot be too short or the intended luer connection to another device will not be secure. The present inventor has determined that a luer length "a" (FIG. 5) of at least about 2.7 mm, preferably about 3.7 mm, most preferably about 4.2 mm, is sufficient to ensure that the connection does not fail during typical applications.

In the preferred embodiment shown, shoulder 27 is formed between first section 25 and second section 26 to define a stepped configuration. Like the first section 25, preferably the second section 26 is tapered so that it narrows in diameter towards its free terminal end 47. This taper assists in the molding operation during manufacture. Preferably the second section 26 has a length of about 3.3 mm and the free terminal end 47 thereof a diameter of about 3.16 mm. If the second section extends too far in the longitudinal axial direction, an insufficient amount of the first section 25, when in the configuration of a male luer, may be available for engagement with a female luer fitting of a receptacle such as a needle, preventing a secure fit. The first and second sections have communicating internal axial bores (shown as 28), preferably centrally located, the diameter of which can vary in accordance with the application. The small outer diameter of the terminal end 47 of the second section 26 relative to the outer diameter of the first section 25 allows the tip of the device to be easily inserted in a small receptacle, such as a standard HPLC vial or even smaller HPLC vial insert, thereby ensuring that the sample being transported to that receptacle is not lost during transfer.

Figure 9:
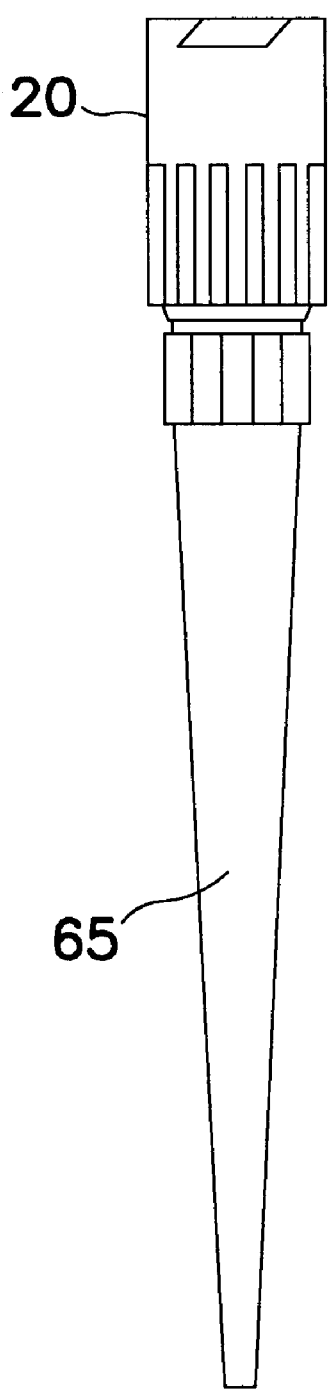
FIG. 9 is a side view of one embodiment of the present invention showing a pipette tip attached to the outlet of the filter device.
Figure 10:
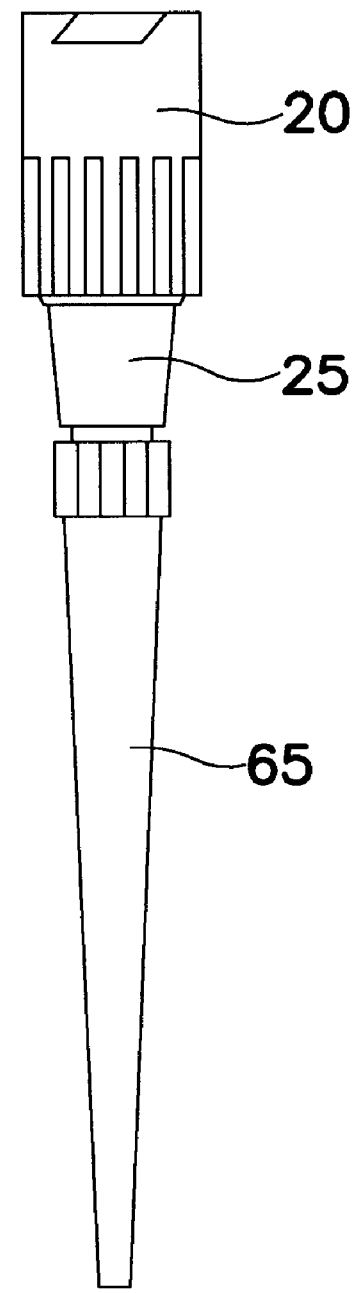
FIG. 10 is a side view of another embodiment of the present invention showing a pipette tip attached to the outlet of the filter device.

In alternative embodiments, the first section 25 is barbed so as to engage a suitable receptacle, or is configured to form a slip fit with the inlet of a pipette tip 65, for example, as shown in FIG. 9. Similarly, the second section 26 could be barbed, or could be configured to form a slip fit with the inlet of a pipette tip 65 as shown in FIG. 10.

Since the filter units of the present invention are generally disposable, they are preferably constructed of an inexpensive thermoplastic material such as a polyolefin, preferably polyethylene or polypropylene. Those skilled in the art will appreciate that other materials of construction are suitable, such as stainless steel, where the economics so allow. A conventional molding operation can be used to form the units, which are preferably one integral piece.

Those skilled in the art will appreciate that the foregoing embodiments utilize generally cylindrical configurations, but that other shapes are within the scope of the present invention. Thus, the inlet and/or the first and/or second sections could have polygonal cross-section, in which case the limitations discussed above with respect to the dimensions of the outside diameters would instead apply to the outside perimeters.

What is claimed is:

1. A filter unit for filtering a sample, comprising a housing for a filter having an inlet, an outlet spaced from said inlet, and a fluid passageway extending therethrough, said outlet comprising an extension extending longitudinally from said housing in the direction of fluid flow, said extension comprising at least a first section having a minimum outer diameter, said first section being dimensioned as a male luer, and a second section downstream from said first section in the direction of fluid flow and having a terminal end having a maximum outer diameter, said maximum outer diameter of said terminal end being smaller than said minimum outer diameter of said first section.

2. The filter unit of claim 1, wherein said housing has a filter having a diameter selected from the group consisting of 4 mm, 13 mm, 25 mm and 50 mm.

3. The filter unit of claim 1, wherein said inlet comprises a female luer section.

4. The filter unit of claim 1, wherein said first section of said extension is barbed.

5. The filter unit of claim 1, wherein said filter unit filters a sample, and said sample to be filtered is housed in a pipette having a terminal pipette tip, and wherein said inlet is configured to form a slip fit with said terminal pipette tip.

6. The filter unit of claim 1, wherein filtrate resulting from filtration of said sample is expelled out said outlet into a container comprising a pipette having a pipette inlet, and wherein said first section of said outlet is configured to form a slip fit with said pipette inlet.

7. The filter unit of claim 1, wherein filtrate resulting from filtration of said sample is expelled out said outlet into a container comprising a pipette having a pipette inlet, and wherein said second section of said outlet is configured to form a slip fit with said pipette inlet.

8. The filter unit of claim 1, wherein the length of said second section in the direction of fluid flow is shorter than the length of said first section in the direction of fluid flow.

9. A filtration device, comprising a housing having filter means supported therein, a fluid inlet to said housing, and a fluid outlet from said housing; said fluid outlet comprising a male luer section having a first axial bore in fluid communication with said housing and having a minimum outside diameter, and a tip portion extending axially from said male luer section, said tip portion having a second axial bore in fluid communication with said first axial bore, said tip portion having an outside diameter smaller than said minimum outside diameter of said male luer section.

10. The filtration device of claim 9, wherein said fluid inlet comprises a female luer section.

11. The filter unit of claim 9, wherein the length of said tip portion in the direction of fluid flow is shorter than the length of said male luer section in the direction of fluid flow.

12. A method of filtering a sample, comprising:

providing a container for said sample, said container comprising a first male luer section;

providing a filter device comprising a housing having a filter, an inlet, an outlet spaced from said inlet, and a fluid passageway extending therethrough, said inlet comprising a female luer section adapted to be removably secured to said first male luer section of said container in a leakproof manner, said outlet comprising a second male luer section having a minimum outside diameter and a tip portion extending axially from said second male luer section and having a terminal end, said terminal end of said tip portion being smaller in outside diameter than said minimum outside diameter of said second male luer section;

providing a receptacle for filtrate;

placing said terminal end of said tip portion in said receptacle; and causing said sample to flow from said container into said housing so as to be filtered by said filter and form a filtrate, said filtrate flowing through said second male luer section and said tip portion into said receptacle.

13. The method of claim 12, wherein said container is a syringe.

14. A filter unit for filtering a sample, comprising a housing for a filter having an inlet, an outlet spaced from said inlet, and a fluid passageway extending therethrough, said outlet comprising an extension extending longitudinally from said housing in the direction of fluid flow, said extension comprising at least a first section having a minimum outer perimeter, said first section being dimensioned as a male luer, and a second section downstream from said first section in the direction of fluid flow and having a terminal end having a maximum outer perimeter, said maximum outer perimeter of said terminal end being smaller than said minimum outer perimeter of said first section.

15. The filter unit of claim 14, wherein the length of said second section in the direction of fluid flow is shorter than the length of said first section in the direction of fluid flow.

* * * * *